(12) United States Patent
Pinel et al.

(10) Patent No.: US 7,507,719 B2
(45) Date of Patent: Mar. 24, 2009

(54) USE OF PEPTIDIC CONJUGATES FOR PREPARING COMPOSITIONS FOR ALOPECIA PREVENTIVE AND CURATIVE TREATMENT

(75) Inventors: Anne-Marie Pinel, Toulouse (FR); Michel Hocquaux, Paris (FR)

(73) Assignee: Institut European De Biologie Cellulaire, Ramonville St. Ange (FR)

( * ) Notice: Subject to any disclaimer, the term of this patent is extended or adjusted under 35 U.S.C. 154(b) by 0 days.

(21) Appl. No.: 10/565,007

(22) PCT Filed: Jul. 16, 2004

(86) PCT No.: PCT/FR2004/001879

§ 371 (c)(1),
(2), (4) Date: Jan. 18, 2006

(87) PCT Pub. No.: WO2005/009456

PCT Pub. Date: Feb. 3, 2005

(65) Prior Publication Data

US 2007/0004633 A1 Jan. 4, 2007

(30) Foreign Application Priority Data

Jul. 18, 2003 (FR) .................... 03 08801

(51) Int. Cl.
*A61K 38/00* (2006.01)
*A61K 51/00* (2006.01)
*A61K 38/04* (2006.01)

(52) U.S. Cl. .................. 514/18; 424/1.89; 530/329; 530/330

(58) Field of Classification Search .............. 514/18
See application file for complete search history.

(56) References Cited

U.S. PATENT DOCUMENTS 5,135,913 A    8/1992  Pickart
5,470,876 A *  11/1995 Proctor .................. 514/492

FOREIGN PATENT DOCUMENTS

| DE | 41 27 790 A | 2/1993 |
|----|-------------|--------|
| EP | 0 293 837 A2 | 12/1988 |
| EP | 0 837 129 A1 | 4/1998 |
| EP | 0 861 266 B1 | 9/1998 |
| EP | 1 008 603 A1 | 6/2000 |
| FR | 2 733 421 A1 | 10/1996 |
| WO | WO-91/07431 A | 5/1991 |
| WO | WO-97/18235 A | 5/1997 |
| WO | WO 9718235 * | 5/1997 |
| WO | WO-00/58347 A | 10/2000 |
| WO | WO-01/98348 A2 | 12/2001 |

OTHER PUBLICATIONS

"Pathologie du cheveu et du cuir chevelu" [Hair and scalp pathology] P. Bouhanna and P. Reygagne- publishers Masson, pp. 14-17 et pp. 51-55.
Philpott et al. 1994, Human Hair growth in vitro: a model for the study of hair biology. Journal of dermatological science 7: S55-S72.
Beck-Piotraschke K et al., Tetrahedron: Asymmetry, Elsevier Science Publishers, amsterdam, NL, vol. 9, No. 9, May 8, 1998, pp. 1505-1518.
Pickart L: In Vitro, Tissue Culture association, US, vol. 17, No. 6, Jun. 1981, pp. 459-466.

\* cited by examiner

*Primary Examiner*—Cecilia Tsang
*Assistant Examiner*—Maury Audet
(74) *Attorney, Agent, or Firm*—Birch, Stewart, Kolasch & Birch, LLP

(57) ABSTRACT

The invention relates to the use of peptidic conjugates containing Gly-His-Lys for producing dermatological or cosmetological compositions for stimulating hair growth or stopping hair fall.

9 Claims, No Drawings

SEQUENCE LISTING

```
<160> NUMBER OF SEQ ID NOS: 19

<210> SEQ ID NO 1
<211> LENGTH: 6
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(3)
<223> OTHER INFORMATION: Xaa is Lys or MeLys and up to two residues
      may be present or absent

<400> SEQUENCE: 1

Xaa Xaa Xaa Gly His Lys
1               5

<210> SEQ ID NO 2
<211> LENGTH: 6
<212> TYPE: PRT
<213> ORGANISM: Artificial sequence
<220> FEATURE:
```

```
<223> OTHER INFORMATION: Description of Artificial Sequence: Synthetic
      peptide
<220> FEATURE:
<221> NAME/KEY: misc_feature
<222> LOCATION: (1)..(3)
<223> OTHER INFORMATION: Xaa is Lys or MeLys and up to two residues
      may be present or absent
<220> FEATURE:
<221> NAME/KEY: MOD_RES
<222> LOCATION: (6)..(6)
<223> OTHER INFORMATION: AMIDATION

<400> SEQUENCE: 2

Xaa Xaa Xaa Gly His Lys
1               5

<210> SEQ ID NO 3
<211> LENGTH: 6
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: BLOCKED
<220> FEATURE:
<221> NAME/KEY: misc_feature
<222> LOCATION: (1)..(3)
<223> OTHER INFORMATION: Xaa is Lys, MeLys, or a bond and up to three
      residues may be  present or absent

<400> SEQUENCE: 3

Xaa Xaa Xaa Gly His Lys
1               5

<210> SEQ ID NO 4
<211> LENGTH: 6
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: BLOCKED
<220> FEATURE:
<221> NAME/KEY: misc_feature
<222> LOCATION: (1)..(3)
<223> OTHER INFORMATION: Xaa is Lys, MeLys, or a bond and up to three
      residues may be present or absent
<220> FEATURE:
<221> NAME/KEY: MOD_RES
<222> LOCATION: (6)..(6)
<223> OTHER INFORMATION: AMIDATION

<400> SEQUENCE: 4

Xaa Xaa Xaa Gly His Lys
1               5

<210> SEQ ID NO 5
<211> LENGTH: 6
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: BLOCKED
```

```
<220> FEATURE:
<221> NAME/KEY: misc_feature
<222> LOCATION: (1)..(1)
<223> OTHER INFORMATION: Xaa = MeLys
<220> FEATURE:
<221> NAME/KEY: MOD_RES
<222> LOCATION: (6)..(6)
<223> OTHER INFORMATION: AMIDATION

<400> SEQUENCE: 5

Xaa Lys Lys Gly His Lys
1               5

<210> SEQ ID NO 6
<211> LENGTH: 5
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: BLOCKED
<220> FEATURE:
<221> NAME/KEY: misc_feature
<222> LOCATION: (1)..(1)
<223> OTHER INFORMATION: Xaa = MeLys
<220> FEATURE:
<221> NAME/KEY: MOD_RES
<222> LOCATION: (5)..(5)
<223> OTHER INFORMATION: AMIDATION

<400> SEQUENCE: 6

Xaa Lys Gly His Lys
1               5

<210> SEQ ID NO 7
<211> LENGTH: 4
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: BLOCKED
<220> FEATURE:
<221> NAME/KEY: misc_feature
<222> LOCATION: (1)..(1)
<223> OTHER INFORMATION: Xaa = MeLys
<220> FEATURE:
<221> NAME/KEY: MOD_RES
<222> LOCATION: (4)..(4)
<223> OTHER INFORMATION: AMIDATION

<400> SEQUENCE: 7

Xaa Gly His Lys
1

<210> SEQ ID NO 8
<211> LENGTH: 6
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: BLOCKED
<220> FEATURE:
```

```
<221> NAME/KEY: misc_feature
<222> LOCATION: (1)..(1)
<223> OTHER INFORMATION: Xaa = MeLys

<400> SEQUENCE: 8

Xaa Lys Lys Gly His Lys
1               5

<210> SEQ ID NO 9
<211> LENGTH: 5
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: BLOCKED
<220> FEATURE:
<221> NAME/KEY: misc_feature
<222> LOCATION: (1)..(1)
<223> OTHER INFORMATION: Xaa = MeLys

<400> SEQUENCE: 9

Xaa Lys Gly His Lys
1               5

<210> SEQ ID NO 10
<211> LENGTH: 4
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: BLOCKED
<220> FEATURE:
<221> NAME/KEY: misc_feature
<222> LOCATION: (1)..(1)
<223> OTHER INFORMATION: Xaa = MeLys

<400> SEQUENCE: 10

Xaa Gly His Lys
1

<210> SEQ ID NO 11
<211> LENGTH: 5
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (5)..(5)
<223> OTHER INFORMATION: AMIDATION

<400> SEQUENCE: 11

Lys Lys Gly His Lys
1               5

<210> SEQ ID NO 12
<211> LENGTH: 4
<212> TYPE: PRT
```

```
<213> ORGANISM: Artificial sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (4)..(4)
<223> OTHER INFORMATION: AMIDATION

<400> SEQUENCE: 12

Lys Gly His Lys
1

<210> SEQ ID NO 13
<211> LENGTH: 5
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: BLOCKED

<400> SEQUENCE: 13

Lys Lys Gly His Lys
1               5

<210> SEQ ID NO 14
<211> LENGTH: 4
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: BLOCKED

<400> SEQUENCE: 14

Lys Gly His Lys
1

<210> SEQ ID NO 15
<211> LENGTH: 11
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(3)
<223> OTHER INFORMATION: Xaa can be Glu-Gln-Arg, Arg-Lys, Arg-Lys-Asp
      sequences or Arg amino acid or a bond and up to 3 residues may be
      present or absent
<220> FEATURE:
<221> NAME/KEY: misc_feature
<222> LOCATION: (7)..(11)
<223> OTHER INFORMATION: Xaa can be Tyr-Val-Gln-Leu-Tyr-Amide, Leu-
      DOPA sequences, the amino acids Dopa amide or HomoPhe amide and
      up to 4 residues may be present or absent

<400> SEQUENCE: 15

Xaa Xaa Xaa Lys Asp Val Xaa Xaa Xaa Xaa Xaa
1               5                   10
```

<210> SEQ ID NO 16
<211> LENGTH: 11
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(3)
<223> OTHER INFORMATION: Xaa can be Gly-Gln-Gln or Glu-Gln sequences
      and up to 1 residue may be present or absent
<220> FEATURE:
<221> NAME/KEY: misc_feature
<222> LOCATION: (7)..(11)
<223> OTHER INFORMATION: Xaa can be Tyr-Val-Gln-Leu-Tyr-Amide, Leu-
      DOPA, Val-Tyr, Val-Tyr-amide sequences, or amino acids Tyr, Tyr
      amide, Dopa amide or HomoPhe amide and up to 4 residues may be
      present or absent

<400> SEQUENCE: 16

Xaa Xaa Xaa Lys Asp Val Xaa Xaa Xaa Xaa Xaa
1               5                   10

<210> SEQ ID NO 17
<211> LENGTH: 11
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: BLOCKED
<220> FEATURE:
<221> NAME/KEY: misc_feature
<222> LOCATION: (1)..(3)
<223> OTHER INFORMATION: Xaa can be Glu-Gln-Arg, Arg-Lys, Arg-Lys-Asp
      sequences or Arg amino acid or a bond and up to 3 residues may
      be present or absent
<220> FEATURE:
<221> NAME/KEY: misc_feature
<222> LOCATION: (7)..(11)
<223> OTHER INFORMATION: Xaa can be Tyr-Val-Gln-Leu-Tyr-Amide, Leu-
      DOPA sequences, amino acids Dopa amide or HomoPhe amide and up to
      4 residues may be present or absent

<400> SEQUENCE: 17

Xaa Xaa Xaa Lys Asp Val Xaa Xaa Xaa Xaa Xaa
1               5                   10

<210> SEQ ID NO 18
<211> LENGTH: 11
<212> TYPE: PRT
<213> ORGANISM: Artificial sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: BLOCKED
<220> FEATURE:
<221> NAME/KEY: misc_feature
<222> LOCATION: (1)..(3)
<223> OTHER INFORMATION: Xaa can be Gly-Gln-Gln or Glu-Gln sequences
      and up to 1 residues may be present or absent
<220> FEATURE:
<221> NAME/KEY: misc_feature
<222> LOCATION: (7)..(11)
<223> OTHER INFORMATION: Xaa can be Tyr-Val-Gln-Leu-Tyr-Amide, Leu-
      DOPA, Val-Tyr, Val-Tyr-amide sequences, or amino acids Tyr, Tyr

```
                                 -continued amide, Dopa amide or HomoPhe amide and up to 4 residues may be
     present or absent

<400> SEQUENCE: 18

Xaa Xaa Xaa Lys Asp Val Xaa Xaa Xaa Xaa Xaa
1               5                   10

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Tyr Val Gln Leu Tyr
1               5
```

USE OF PEPTIDIC CONJUGATES FOR PREPARING COMPOSITIONS FOR ALOPECIA PREVENTIVE AND CURATIVE TREATMENT

The invention relates to the use of peptide conjugates containing the sequence Gly-His-Lys, for preparing dermatological or cosmetic compositions for stimulating hair growth or slowing down hair loss.

Throughout the life of an individual, hair growth and hair renewal are determined by the activity of the hair follicles. They perform a regular cycle made up of three phases: anagen, catagen and telogen, which are each characterized by very specific molecular and cellular mechanisms:

During the anagen phase which lasts approximately three years, the cells of the dermal papilla "send" signals to the stem cells present in the bulb. The competent cells that receive these signals then migrate to the hair follicle matrix; these are then referred to as matrix cells. In this region, the cells of the dermal papilla emit additional signals which allow the matrix cells to firstly proliferate and then to differentiate, which allows elongation of the hair shaft. During this phase, the hair follicle migrates through the dermis so as to be, in anagen VI, anchored in the hypodermis in contact with the adipose tissue.

The phase that follows, called catagen, is a short phase which lasts approximately three weeks, during which the cells of the lower part of the hair follicle enter into apoptosis, thus allowing degeneration of the hair follicle.

The remaining phase, referred to as telogen, is a lag phase characterized by inactivity of the hair follicle for three months and loss of the hair before a further entry into the anagen phase.

Since appearance is, in this day and age, an essential social factor, hair loss is a real problem which can be experienced as a social handicap by certain individuals. In man, it involves in most cases androgenic alopecia. This type of alopecia is therefore due to a deficiency in the catabolism of androgens, and more specifically of testosterone in the hair follicle by the dermal papilla cells. In fact, there is accumulation of a testosterone metabolite, DHT (a metabolite which is produced by the action of 5α-reductase on testosterone), in the hair follicles. In a normal process, this compound is degraded and then eliminated in the urine. At the current time, 5α-reductase inhibitors are used in this type of alopecia in order to slow down hair loss.

All the current knowledge concerning the biology of the hair and of the scalp, types of alopecia and conditions of the scalp, and their treatments are given in: "Pathologie du cheveu et du cuir chevelu" [Hair and scalp pathology] P. Bouhanna and P. Reygagne—publishers Masson.

For many years, in the cosmetics or pharmaceutical industry, there has been a continuing search for substances that make it possible to eliminate or reduce the effect of alopecia, and in particular to induce or stimulate hair growth or to decrease hair loss.

A certain number of compounds are already used, such as minoxidil or finasteride.

Some peptides are known for their stimulatory action on hair growth; however, no document discloses the fact that the peptide conjugates described hereinafter are useful in the preventive and curative treatment of alopecia.

A subject of the present invention is therefore the use of a peptide corresponding to general formula (I)

X-Gly-His-Lys-Y      (I)      (SEQ ID Nos. 1-2)

or of the conjugate thereof corresponding to general formula (II)

A-X-Gly-His-Lys-Y    (II)     (SEQ ID Nos. 3-4)

in which
  A represents the radical corresponding to
  a monocarboxylic acid of general formula (III)

HOOC—R                                        (III)

in which
  R represents a linear or branched $C_1$-$C_{24}$ aliphatic radical optionally substituted with a hydroxyl group, possibly containing one or more unsaturations, advantageously from 1 to 6,
    lipoic acid or its reduced form, dihydrolipoic acid, N-lipoyl-lysine or else retinoic acid,
  X represents a chain of 1 to 3 Lys residues, that are optionally methylated, or, when the formula is formula (II), a bond,
  Y represents an —OH or —$NH_2$ group,
  the amino acids being in D, L or DL form,
  or else A-X represents a hydrogen atom, for preparing a cosmetic or dermatological composition for use in the preventive and curative treatment of alopecia.

Advantageously, the peptide sequence is chemically or physically conjugated with the acids A. The conjugated peptides according to the invention are bonded in the form of salts, of esters, or of amides to these acids A, the carboxylic acid fraction of the acid providing the bond.

The amino acids in the peptide of formula (I) or the peptide conjugate of formula (II) may have a D, L or DL configuration.

In other words, the peptides of formula (I) and the peptide conjugates of formula (II) can contain one or more asymmetrical carbon atoms. They can therefore exist in the form of enantiomers or of diastereoisomers. These enantiomers and diastereoisomers, and also the mixtures thereof, including racemic mixtures, are part of the invention.

The peptide conjugates of formula (II) are low-molecular-weight derivatives which are obtained in the form of amides of the compound of formula (III).

In addition, the peptides of formula (I) and the peptide conjugates of formula (II) can be coupled with zinc, in the form of salts, so as to form complexes.

The peptides and the peptide conjugates thereof, and also the synthesis thereof, are described in European Patent EP 869 969. They are described therein as being useful in the treatment, by topical application, of chronic wound healing, esthetic healing of surgical wounds, and the preventive and curative treatment of stretch marks and of complications thereof. Their use in the cosmetology field, in particular in the preventive and curative treatment of wrinkles on the face, the neck and the hands, is also disclosed therein.

In the context of the present invention:
  the term "Lys" is intended to mean lysine or a halogenated derivative of lysine, such as dihydrobromomethyllysine,
  the term "MeLys" is intended to mean methyllysine (methylation in the 6-position),
  the term "His" is intended to mean histidine, the term "Gly" is intended to mean glycine or an alkylated derivative thereof, such as methylglycine.

It is also specified that the peptides of formula (I) or the peptide conjugates of formula (II) mentioned above, and the use of which is the subject of the present invention, can be obtained in the $NH_2$-terminal form (in other words, exhibiting an amide function) and in the OH-terminal form (in other words, exhibiting a carboxylic acid function).

Preferably, the acid of formula (III) is a polyunsaturated fatty acid, i.e. containing from 1 to 6 unsaturations. Even more preferably, it is an omega-3 acid.

Among these omega-3 acids, mention may in particular be made of α-linolenic acid, cervonic acid, timnodonic acid and pinolenic acid. Cervonic acid, timnodonic acid and pinolenic acid are also known under the respective names: 4,7,10,13, 16,19-docosahexaenoic acid (DHA), 5,8,11,14,17-eicosapentaenoic acid (EPA) and 5,9,12-octodecatrienoic acid.

When A represents a monocarboxylic acid of general formula (III), it may be advantageously chosen from acetic acid, myristic acid, palmitic acid, and hydroxy-decenoic and decenoic acids, and in particular trans-10-hydroxy-Δ2-decenoic acid and trans-oxo-9-decen-2-oic acid.

Among the peptide conjugates of the invention, mention may be made of the following peptide conjugates:

```
1-
A-MeLys-Lys-Lys-Gly-His-Lys-NH2,    (SEQ ID No. 5)
2-
A-MeLys-Lys-Gly-His-Lys-NH2,        (SEQ ID No. 6)
3-
A-MeLys-Gly-His-Lys-NH2,            (SEQ ID No. 7)
4-
A-MeLys-Lys-Lys-Gly-His-Lys-OH,     (SEQ ID No. 8)
5-
A-MeLys-Lys-Gly-His-Lys-OH,         (SEQ ID No. 9)
6-
A-MeLys-Gly-His-Lys-OH,             (SEQ ID No. 10)
7-
A-Lys-Lys-Gly-His-Lys-NH2,          (SEQ ID No. 11)
8-
A-Lys-Gly-His-Lys-NH2,              (SEQ ID No. 12)
9-
A-Lys-Lys-Gly-His-Lys-OH,           (SEQ ID No. 13)
10-
A-Lys-Gly-His-Lys-OH.               (SEQ ID No. 14)
```

The peptide conjugates for which A is chosen from lipoic acid and acetic acid are most particularly suitable in the context of the present invention.

Mention may also be made of the following peptide conjugates:

```
Peptide R    H-Gly-His-Lys-OH,
Peptide S    Lipoyl-Lys-Gly-His-Lys-NH2,
             (SEQ ID NO: 12)
Peptide V    Ac-Lys-Gly-His-Lys-NH2.
             (SEQ ID NO: 12)
```

The peptides or the peptide conjugates thereof can be administered topically for their cosmetic use.

They can also be used orally in food supplements, in other words in the nutraceutic field.

They are preferably administered topically.

The peptide conjugate may be present, in a topical cosmetic composition, at a concentration of between $10^{-8}$ and $10^{-3}$ M, preferably of between $10^{-7}$ and $10^{-5}$ M.

The cosmetic or dermatological composition may, for example, be in the form of a lotion, of a treating shampoo, of a spray, of a gel or of a treating cream.

Another subject of the present invention concerns the method of cosmetic treatment for combating hair loss, comprising the application to the scalp of a composition comprising a peptide conjugate as described above, optionally in combination as described hereinafter.

They can be administered alone or in combination with compounds that further enhance the activity on regrowth and that have already been described for this activity.

Among these compounds, mention may be made of:
minoxidil,
nicotinic acid esters,
anti-inflammatory agents, more particularly peptides with anti-inflammatory activity,
retinoic acid, derivatives thereof and retinol,
5α-reductase inhibitors.

Other peptides or peptide conjugates can also be combined with the peptides or peptide conjugates whose use is the subject of the present invention. They correspond to the formulae W-Lys-Asp-Val-Z      (I)      (SEQ ID Nos. 15-16)

or the peptide conjugate thereof corresponding to formula (II)

A-W-Lys-Asp-Val-Z    (II)     (SEQ ID Nos. 17-18)

in which A has the same definition as that given above,
and W represents
Glu-Gln-Arg, Arg-Lys, Arg-Lys-Asp, Arg or a bond,
when Z represents
Tyr-Val-Gln-Leu-Tyr-$NH_2$(SEO ID NO: 19), Leu-DOPA, DOPA-$NH_2$ or HomoPhe-NH2,
or else W represents Gly-Gln-Gln or Glu-Gln,
when Z represents
Tyr-Val-Gln-Leu-Tyr-$NH_2$(SEO ID NO: 19), Leu-DOPA, Val-Tyr-OH,
Val-Tyr-$NH_2$, Tyr-$NH_2$, Tyr-OH, DOPA-$NH_2$ or HomoPhe-$NH_2$, in the form of enantiomers or of diastereoisomers, and also the mixtures thereof, including racemic mixtures, and the complexes with zinc which can be formed with these peptides or peptide conjugates.

The term "DOPA" is intended to mean dihydroxyphenylalanine and the term "HomoPhe" is intended to mean homophenylalanine.

Finally, one or more UVB-screening agents can also be combined with the peptides or with the peptide conjugates whose use is the subject of the present invention, when a topical administration is involved. They allow photoprotection of the scalp. Thus, among suitable UVB-screening agents, mention may be made, given as their INCI name, of:
p-aminobenzoic acid or PABA and its esters:
Ethylhexyl dimethylPABA
PEG-25 PABA
cinnamates:
Ethylhexyl methoxycinnamate
Isoamyl p-methoxycinnamate
Octoacrylene salicylates:
  Homosalate
  Ethylhexyl salicylate
benzimidazoles:
  Phenylbenzimidazolesulfonic acid
benzylidenecamphor derivatives
  4-Methylbenzylidenecamphor
  Benzylidenecamphor
  Camphor benzalkonium methosulfate
  Polyacrylamidomethylbenzylidenecamphor
triazines:
  Ethylhexyl triazone
  Diethylhexyl butamido triazone.

The peptides and peptide conjugates whose use is the subject of the invention were the subject of pharmacological trials making it possible to show their anti-hair loss activity.

Effects of the Various Peptides on the Growth of Mouse Vibrissae In Vitro

In order to show the stimulatory effect of the peptides on hair growth, anagen-phase hair follicles of mouse vibrissae are cultured according to the technique described by Philpott (Philpott et al. 1994, *Human Hair growth in vitro: a model for the study of hair biology*. Journal of dermatological science 7; S55-S72). The growth of the hair follicle shaft was followed for several days (D0 to D4). The results are reported in the table below for the peptides R, S and V described above. These results show that these peptides stimulate hair growth when the hair follicles are kept alive in vitro.

|    | Control | Peptide R $10^{-7}$ M | Peptide S $10^{-7}$ M | Peptide V $10^{-7}$ M |
|----|---------|-----------------------|-----------------------|-----------------------|
| D0 | 0.00    | 0.00                  | 0.00                  | 0.00                  |
| D1 | 0.3     | 0.8                   | 0.77                  | 0.86                  |
| D2 | 0.4     | 1.27                  | 1.47                  | 1.34                  |
| D3 | 0.5     | 1.38                  | 1.72                  | 1.65                  |
| D4 | 0.5     | 1.38                  | 1.86                  | 1.65                  |

The following formulation examples illustrate the present invention.

EXAMPLE 1

Lotion Comprising the Peptide Conjugate Ac-Lys-Gly-His-Lys-NH$_2$ (SEQ ID NO: 12)

|                                                    | (in g)             |
|----------------------------------------------------|--------------------|
| Peptide Ac-Lys-Gly-His-Lys-NH$_2$                  | $5 \times 10^{-6}$ |
| 95° ethanol                                        | 60                 |
| Propylene glycol                                   | 10                 |
| Water - preserving agents - fragrance              | qs 100             |

EXAMPLE 2

Lotion Comprising the Peptide Conjugate Lipoyl-Lys-Gly-His-Lys-NH$_2$ (SEQ ID NO:12)

|                                              | (in g)     |
|----------------------------------------------|------------|
| Peptide Lipoyl-Lys-Gly-His-Lys-NH$_2$        | $10^{-5}$  |
| Water                                        | 81         |
| Keltrol T                                    | 0.5        |
| Techpolymer MB-4C                            | 1          |
| Sepigel 305                                  | 0.5        |
| Silicone oil 0.2 1401                        | 2          |
| Butylene glycol                              | 5          |

The invention claimed is:

1. A method for the treatment of alopecia or hair-loss comprising the administration to a patient in need thereof of a composition comprising:

a therapeutically effective amount of a peptide conjugate which is not coupled with zinc and which is represented by general formula (II)

A-X-Gly-His-Lys-Y    (II)    (SEQ ID Nos. 3-4)

wherein,

A represents the radical represented by to a monocarboxylic acid of general formula (III)

HOOC—R    (III)

wherein, R represents a linear or branched $C_1$-$C_{24}$ aliphatic radical optionally substituted with a hydroxyl group, possibly containing one or more unsaturations, Lipoic acid or its reduced form, dihydrolipoic acid, N-lipoyl-lysine or retinoic acid, X represents 1 to 3 Lys residues, that are optionally methylated, or a bond, and Y represents an —OH or —$NH_2$ group, the amino acids being in D, L or DL form.

2. The method as claimed in claim 1, wherein the acid of general formula (III) is an omega-3 acid selected from the group consisting of α-linolenic acid, cervonic acid, timnodonic acid and pinolenic acid or a $C_1$-$C_{24}$ aliphatic radical selected from the group consisting of acetic acid, myristic acid, palmitic acid, and hydroxydecenoic and decenoic acids, or an acid selected from the group consisting of lipoic acid or its reduced form, dihydrolipoic acid, N-lipoyl-lysine and retinoic acid.

3. The method as claimed in claim 2, wherein A is lipoic acid or acetic acid.

4. The method as claimed in claim 1, wherein the peptide conjugate of formula II is selected from the group consisting of the peptide conjugates of the following formula:

```
1-
A-MeLys-Lys-Lys-Gly-His-Lys-NH2,    (SEQ ID No. 5)

2-
A-MeLys-Lys-Gly-His-Lys-NH2,        (SEQ ID No. 6)

3-
A-MeLys-Gly-His-Lys-NH2,            (SEQ ID No. 7)

4-
A-MeLys-Lys-Lys-Gly-His-Lys-OH,     (SEQ ID No. 8)

5-
A-MeLys-Lys-Gly-His-Lys-OH,         (SEQ ID No. 9)

6-
A-MeLys-Gly-His-Lys-OH,             (SEQ ID No. 10)

7-
A-Lys-Lys-Gly-His-Lys-NH2,          (SEQ ID No. 11)

8-
A-Lys-Gly-His-Lys-NH2,              (SEQ ID No. 12)

9-
A-Lys-Lys-Gly-His-Lys-OH,           (SEQ ID No. 13)

10-
A-Lys-Gly-His-Lys-OH,               (SEQ ID No. 14)
```

A being an acid of general formula (III) as defined in claim 1.

5. The method as claimed in claim 1, wherein the peptide conjugate of formula II is chosen from:

```
Lipoyl-Lys-Gly-His-Lys-NH2, or    (SEQ ID NO:12)

Ac-Lys-Gly-His-Lys-NH2.           (SEQ ID NO:12)
```

6. The method as claimed in claim 1, wherein said composition further comprises a compound that improves hair regrowth, selected from the group consisting of minoxidil, nicotinic acid esters, anti-inflammatory agents, retinoic acid or derivatives thereof, retinol and 5α-reductase inhibitors.

7. The method as claimed in claim 1, wherein the administration is made by topical route and wherein said composition further comprises a UVB-screening agent selected from the group consisting of p-aminobenzoic acid (PABA) and esters thereof, cinnamates, salicylates, benzimidazoles, benzylidenecamphor derivatives, and triazines.

8. The method as claimed in claim 1, wherein the administration is an application to the scalp of the patient.

9. The method as claimed in claim 1, wherein the peptide conjugate of formula (II) is present at a concentration of between $10^{-8}$ and $10^{-3}$ M of the total concentration.

* * * * *

UNITED STATES PATENT AND TRADEMARK OFFICE
CERTIFICATE OF CORRECTION

PATENT NO. : 7,507,719 B2
APPLICATION NO. : 10/565007
DATED : March 24, 2009
INVENTOR(S) : Anne-Marie Pinel et al.

It is certified that error appears in the above-identified patent and that said Letters Patent is hereby corrected as shown below:

Title page item [73]

"Institut European De Biologie Cellulaire" should read --Institut Europeen De Biologie Cellulaire--.

Signed and Sealed this

Fifteenth Day of June, 2010

David J. Kappos
*Director of the United States Patent and Trademark Office*